(12) United States Patent
Johansson et al.

(10) Patent No.: US 9,657,055 B2
(45) Date of Patent: May 23, 2017

(54) AFFINITY CHROMATOGRAPHY MATRIX

(71) Applicant: GE Healthcare BioProcess R&D AB, Uppsala (SE)

(72) Inventors: Hans J. Johansson, Uppsala (SE); Ronnie Palmgren, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 226 days.

(21) Appl. No.: 14/358,821

(22) PCT Filed: Nov. 28, 2012

(86) PCT No.: PCT/SE2012/051316
§ 371 (c)(1),
(2) Date: May 16, 2014

(87) PCT Pub. No.: WO2013/081540
PCT Pub. Date: Jun. 6, 2013

(65) Prior Publication Data
US 2014/0329995 A1 Nov. 6, 2014

(30) Foreign Application Priority Data
Nov. 30, 2011 (SE) ...................................... 1151137

(51) Int. Cl.
| | | |
|---|---|---|
| *B01D 15/38* | (2006.01) | |
| *C07K 1/22* | (2006.01) | |
| *C07K 14/31* | (2006.01) | |
| *C07K 19/00* | (2006.01) | |
| *B01J 20/286* | (2006.01) | |
| *B01J 20/32* | (2006.01) | |
| *C07K 14/245* | (2006.01) | |
| *B01D 15/34* | (2006.01) | |

(52) U.S. Cl.
CPC ............ *C07K 1/22* (2013.01); *B01D 15/3809* (2013.01); *B01J 20/286* (2013.01); *B01J 20/3274* (2013.01); *C07K 14/245* (2013.01); *C07K 14/31* (2013.01); *B01D 15/34* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 7,709,209 | B2 * | 5/2010 | Hober ................. | C07K 16/065 435/7.1 |
| 2010/0221844 | A1 * | 9/2010 | Bian ................. | B01D 15/3809 436/501 |
| 2013/0274451 | A1 * | 10/2013 | Bjorkman .......... | B01D 15/3809 530/389.5 |

FOREIGN PATENT DOCUMENTS

| | | | |
|---|---|---|---|
| CN | 101337986 | 1/2009 | |
| CN | 101337986 A | 1/2009 | |
| CN | 101760466 | 6/2010 | |
| CN | 101760466 B | 12/2015 | |
| EP | 0863210 | 9/1998 | |
| EP | 2202310 | 6/2010 | |
| EP | 2412809 | 2/2012 | |
| EP | 2532672 | 12/2012 | |
| JP | EP 0261679 A2 * | 3/1988 | ............ C08G 8/36 |
| JP | EP 0550771 A1 * | 7/1993 | ............ C07K 14/31 |
| JP | 2008255046 | 10/2008 | |
| JP | 2008255046 A | 10/2009 | |
| WO | WO 03/080655 | 10/2003 | |
| WO | WO 2007019376 A2 * | 2/2007 | .......... A61K 49/085 |
| WO | WO 2008/039141 | 4/2008 | |
| WO | WO 2012/086660 | 6/2012 | |
| WO | WO 2012/087231 | 6/2012 | |

OTHER PUBLICATIONS

Ljungberg, U., et al., Molecular Immunology, vol. 30, No. 14, 1993, pp. 1279-1285.

* cited by examiner

*Primary Examiner* — Daniel E Kolker
*Assistant Examiner* — James Rogers
(74) *Attorney, Agent, or Firm* — Wood IP LLC

(57) ABSTRACT

The invention discloses a polypeptide capable of binding immunoglobulins or immunoglobulin-containing proteins, which polypeptide comprises six or more domains of protein Z or the C domain of protein A or a functional variant thereof. It also discloses separation matrices comprising the polypeptide and methods of using the separation matrices for separation of immunoglobulins or immunoglobulin-containing proteins.

21 Claims, 1 Drawing Sheet

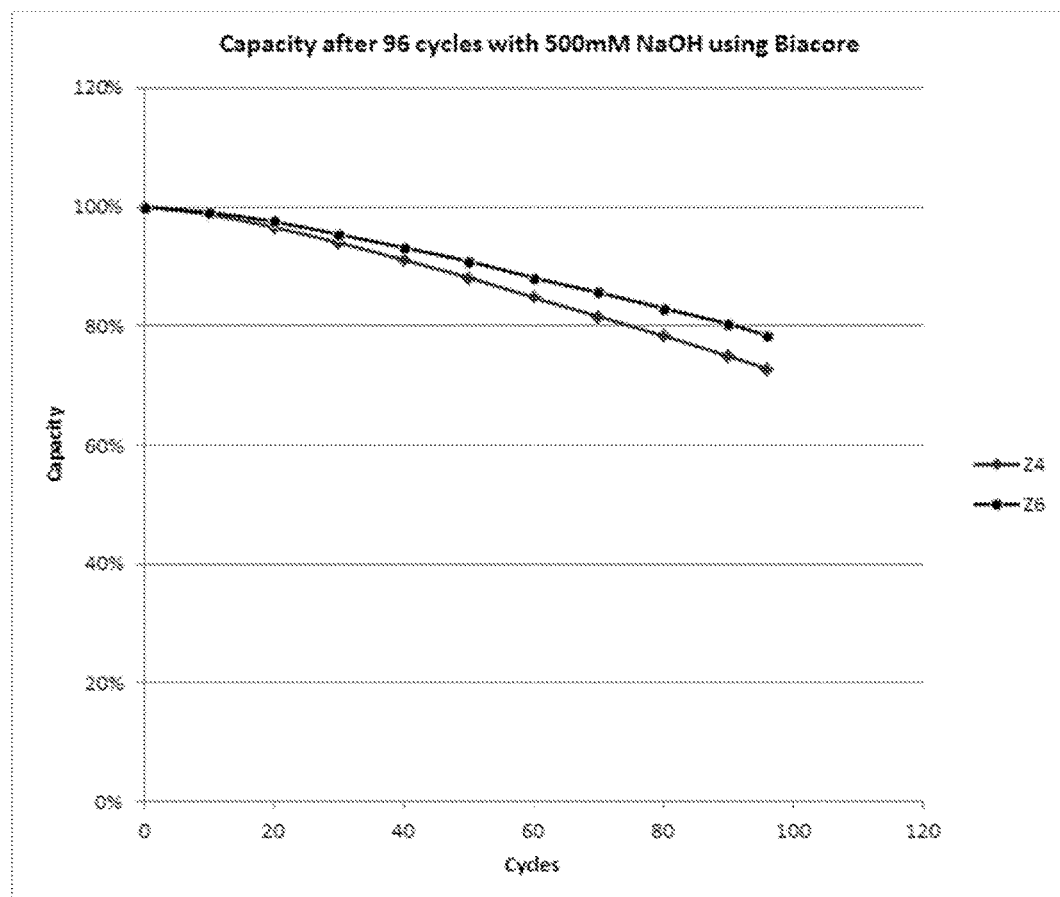

SEQUENCE LISTING

```
<160> NUMBER OF SEQ ID NOS: 12

<210> SEQ ID NO 1
<211> LENGTH: 58
<212> TYPE: PRT
<213> ORGANISM: Escherichia coli

<400> SEQUENCE: 1

Val Asp Ala Lys Phe Asp Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
```

```
<212> TYPE: PRT
<213> ORGANISM: Escherichia coli

<400> SEQUENCE: 2

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 3
<211> LENGTH: 237
<212> TYPE: PRT
<213> ORGANISM: Escherichia coli

<400> SEQUENCE: 3

Ala Gln Gly Thr Val Asp Ala Lys Phe Asp Lys Glu Gln Gln Asn Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Gln Ser Ala Asn Leu
        35                  40                  45

Leu Ala Glu Ala Lys Lys Leu Asn Asp Ala Gln Ala Pro Lys Val Asp
    50                  55                  60

Ala Lys Phe Asp Lys Glu Gln Gln Asn Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Asp Pro Ser Gln Ser Ala Asn Leu Leu Ala Glu Ala Lys Lys
            100                 105                 110

Leu Asn Asp Ala Gln Ala Pro Lys Val Asp Ala Lys Phe Asp Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Gln
145                 150                 155                 160

Ser Ala Asn Leu Leu Ala Glu Ala Lys Lys Leu Asn Asp Ala Gln Ala
                165                 170                 175

Pro Lys Val Asp Ala Lys Phe Asp Lys Glu Gln Gln Asn Ala Phe Tyr
            180                 185                 190

Glu Ile Leu His Leu Pro Asn Leu Thr Glu Glu Gln Arg Asn Ala Phe
        195                 200                 205

Ile Gln Ser Leu Lys Asp Asp Pro Ser Gln Ser Ala Asn Leu Leu Ala
    210                 215                 220

Glu Ala Lys Lys Leu Asn Asp Ala Gln Ala Pro Lys Cys
225                 230                 235

<210> SEQ ID NO 4
<211> LENGTH: 353
<212> TYPE: PRT
<213> ORGANISM: Escherichia coli

<400> SEQUENCE: 4

Ala Gln Gly Thr Val Asp Ala Lys Phe Asp Lys Glu Gln Gln Asn Ala
```

```
                1               5                   10                  15
            Phe Tyr Glu Ile Leu His Leu Pro Asn Leu Thr Glu Glu Gln Arg Asn
                            20                  25                  30

Ala Phe Ile Gln Ser Leu Lys Asp Asp Pro Ser Gln Ser Ala Asn Leu
                            35                  40                  45

Leu Ala Glu Ala Lys Lys Leu Asn Asp Ala Gln Ala Pro Lys Val Asp
            50                      55                  60

Ala Lys Phe Asp Lys Glu Gln Gln Asn Ala Phe Tyr Glu Ile Leu His
            65                      70                  75                  80

Leu Pro Asn Leu Thr Glu Glu Gln Arg Asn Ala Phe Ile Gln Ser Leu
                            85                  90                  95

Lys Asp Asp Pro Ser Gln Ser Ala Asn Leu Leu Ala Glu Ala Lys Lys
                            100                 105                 110

Leu Asn Asp Ala Gln Ala Pro Lys Val Asp Ala Lys Phe Asp Lys Glu
                            115                 120                 125

Gln Gln Asn Ala Phe Tyr Glu Ile Leu His Leu Pro Asn Leu Thr Glu
                    130                 135                 140

Glu Gln Arg Asn Ala Phe Ile Gln Ser Leu Lys Asp Asp Pro Ser Gln
            145                     150                 155                 160

Ser Ala Asn Leu Leu Ala Glu Ala Lys Lys Leu Asn Asp Ala Gln Ala
                            165                 170                 175

Pro Lys Val Asp Ala Lys Phe Asp Lys Glu Gln Gln Asn Ala Phe Tyr
                            180                 185                 190

Glu Ile Leu His Leu Pro Asn Leu Thr Glu Glu Gln Arg Asn Ala Phe
                            195                 200                 205

Ile Gln Ser Leu Lys Asp Asp Pro Ser Gln Ser Ala Asn Leu Leu Ala
            210                     215                 220

Glu Ala Lys Lys Leu Asn Asp Ala Gln Ala Pro Lys Val Asp Ala Lys
            225                     230                 235                 240

Phe Asp Lys Glu Gln Gln Asn Ala Phe Tyr Glu Ile Leu His Leu Pro
                            245                 250                 255

Asn Leu Thr Glu Glu Gln Arg Asn Ala Phe Ile Gln Ser Leu Lys Asp
                            260                 265                 270

Asp Pro Ser Gln Ser Ala Asn Leu Leu Ala Glu Ala Lys Lys Leu Asn
                            275                 280                 285

Asp Ala Gln Ala Pro Lys Val Asp Ala Lys Phe Asp Lys Glu Gln Gln
                            290                 295                 300

Asn Ala Phe Tyr Glu Ile Leu His Leu Pro Asn Leu Thr Glu Glu Gln
            305                     310                 315                 320

Arg Asn Ala Phe Ile Gln Ser Leu Lys Asp Asp Pro Ser Gln Ser Ala
                            325                 330                 335

Asn Leu Leu Ala Glu Ala Lys Lys Leu Asn Asp Ala Gln Ala Pro Lys
                            340                 345                 350

Cys

<210> SEQ ID NO 5
<211> LENGTH: 48
<212> TYPE: PRT
<213> ORGANISM: Escherichia coli

<400> SEQUENCE: 5

Lys Glu Gln Gln Asn Ala Phe Tyr Glu Ile Leu His Leu Pro Asn Leu
1               5                   10                  15

Asn Glu Glu Gln Arg Asn Ala Phe Ile Gln Ser Leu Lys Asp Asp Pro
```

```
                     20                  25                  30

Ser Gln Ser Ala Asn Leu Leu Ala Glu Ala Lys Lys Leu Asn Asp Ala
             35                  40                  45

<210> SEQ ID NO 6
<211> LENGTH: 48
<212> TYPE: PRT
<213> ORGANISM: Escherichia coli

<400> SEQUENCE: 6

Lys Glu Gln Gln Asn Ala Phe Tyr Glu Ile Leu His Leu Pro Asn Leu
1               5                   10                  15

Thr Glu Glu Gln Arg Asn Ala Phe Ile Gln Ser Leu Lys Asp Asp Pro
             20                  25                  30

Ser Gln Ser Ala Asn Leu Leu Ala Glu Ala Lys Lys Leu Asn Asp Ala
             35                  40                  45

<210> SEQ ID NO 7
<211> LENGTH: 48
<212> TYPE: PRT
<213> ORGANISM: Staphylococcus aureus

<400> SEQUENCE: 7

Lys Glu Gln Gln Asn Ala Phe Tyr Glu Ile Leu His Leu Pro Asn Leu
1               5                   10                  15

Thr Glu Glu Gln Arg Asn Gly Phe Ile Gln Ser Leu Lys Asp Asp Pro
             20                  25                  30

Ser Val Ser Lys Glu Ile Leu Ala Glu Ala Lys Lys Leu Asn Asp Ala
             35                  40                  45

<210> SEQ ID NO 8
<211> LENGTH: 58
<212> TYPE: PRT
<213> ORGANISM: Staphylococcus aureus

<400> SEQUENCE: 8

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
             20                  25                  30

Ser Leu Lys Asp Asp Pro Ser Val Ser Lys Glu Ile Leu Ala Glu Ala
             35                  40                  45

Lys Lys Leu Asn Asp Ala Gln Ala Pro Lys
         50                  55

<210> SEQ ID NO 9
<211> LENGTH: 6
<212> TYPE: PRT
<213> ORGANISM: Artificial Sequence
<220> FEATURE:
<223> OTHER INFORMATION: Linker

<400> SEQUENCE: 9

Val Asp Ala Lys Phe Asp
1               5

<210> SEQ ID NO 10
<211> LENGTH: 6
<212> TYPE: PRT
<213> ORGANISM: Artificial Sequence
<220> FEATURE:
<223> OTHER INFORMATION: Linker
```

```
<400> SEQUENCE: 10

Val Asp Ala Lys Phe Asn
1               5

<210> SEQ ID NO 11
<211> LENGTH: 10
<212> TYPE: PRT
<213> ORGANISM: Artificial Sequence
<220> FEATURE:
<223> OTHER INFORMATION: Linker

<400> SEQUENCE: 11

Gln Ala Pro Lys Val Asp Ala Lys Phe Asp
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Linker

<400> SEQUENCE: 12

Gln Ala Pro Lys Val Asp Ala Lys Phe Asn
1               5                   10
```

AFFINITY CHROMATOGRAPHY MATRIX

CROSS-REFERENCE TO RELATED APPLICATIONS

This application is a filing under 35 U.S.C. 371 of international application No. PCT/SE2012/051316, filed Nov. 28, 2012, published on Jun. 6, 2013 as WO 2013/081540, which claims priority to application No. 1151137-5 filed in Sweden on Nov. 30, 2011.

STATEMENT REGARDING SEQUENCE LISTING

The Sequence Listing associated with this application is part of the description and is provided in text the form of an Annex C/ST.25 text file in lieu of a paper copy, and is hereby incorporated by reference into the specification. The name of the text file containing the Sequence Listing is 253126_SequenceListing_ST25.txt. The text file is 10kb, was created on Aug. 17, 2016, and is being submitted electronically via EFS-Web.

TECHNICAL FIELD OF THE INVENTION

The present invention relates to the field of affinity chromatography, and more specifically to a separation matrix containing ligands comprising multimers of Protein Z or the C domain of Protein A. The invention also relates to methods for the separation of proteins of interest with aforementioned matrix, with the advantage of increased capacity and alkali stability.

BACKGROUND OF THE INVENTION

Immunoglobulins represent the most prevalent biopharmaceutical products in either manufacture or development worldwide. The high commercial demand for and hence value of this particular therapeutic market has led to the emphasis being placed on pharmaceutical companies to maximize the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A SEPHAROSE™, GE Healthcare). More specifically, the genetic manipulation performed in the commercial recombinant protein A product is aimed at facilitating the attachment thereof to a support.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitizing agent is NaOH, and the concentration thereof can range from 0.1 up to e.g. 1 M, depending on the degree and nature of contamination. This strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focused on the development of engineered protein ligands that exhibit an improved capacity to withstand alkaline pH-values. For example, Gülich et al. (Susanne Gülich, Martin Linhult, Per-Åke Nygren, Mathias Uhlén, Sophia Hober, Journal of Biotechnology 80 (2000), 169-178) suggested protein engineering to improve the stability properties of a Streptococcal albumin-binding domain (ABD) in alkaline environments. Gülich et al. created a mutant of ABD, wherein all the four asparagine residues have been replaced by leucine (one residue), aspartate (two residues) and lysine (one residue). Further, Gülich et al. report that their mutant exhibits a target protein binding behavior similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work shows that changes can also be made to protein A (SpA) to effect similar properties. US patent application publication US 2005/0143566 discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844). The authors show that when these mutated proteins are used as affinity ligands, the separation media as expected can better withstand cleaning procedures using alkaline agents. US 2006/0194955 shows that the mutated ligands can better withstand proteases thus reducing ligand leakage in the separation process. Another publication, US 2006/0194950 shows that the alkali stable SpA domains can be further modified such that the ligands lacks affinity for Fab but retains Fc affinity, for example by a G29A mutation.

In order to decrease the replacement cost of affinity chromatography media, there is a strong desire from the bioprocessing industry to increase the number of cycles an affinity column can be used. This means that stability towards a large number of separation cycles, each involving treatment with 0.1-1 M sodium hydroxide, is a highly desirable property for a protein A product. Hence, there is still a need to further improve the alkali stability of ligands based on protein A domains or mutations of protein A domains.

Historically the native protein A containing 5 IgG binding domains was used for production of all protein A affinity media. Using recombinant technology a number of protein A constructs have been produced all containing 4 or 5 IgG binding domains. A recent study showed that dimeric ligands have a similar, or increased binding capacity compared to tetrameric ligands (WO 2010/080065). CN101337986 discloses a specific hexamer of Protein A B-domains with A1V and A1L mutations. The binding capacity of this hexamer is however low (in the order of 30 mg/ml).

There is still a need in this field to obtain a separation matrix containing protein ligands having an increased binding capacity.

SUMMARY OF THE INVENTION

One aspect of the invention is to provide a polypeptide able to bind large amounts of immunoglobulins. This is achieved with a polypeptide as defined in claim 1.

One advantage is that the ligand has a high binding capacity for immunoglobulins. A further advantage is that it has an improved alkali stability.

Another aspect of the invention is to provide a separation matrix with high capacity for immunoglobulins. This is achieved with a matrix as defined in claim 10.

A third aspect of the invention is to provide an efficient method of separating immunoglobulins. This is achieved by a method as defined in claim 17.

Further suitable embodiments of the invention are described in the dependent claims.

BRIEF DESCRIPTION OF THE FIGURES

FIG. 1 shows the long-term alkali stability of hexamers according to the invention, as compared with reference tetramers.

DETAILED DESCRIPTION OF EMBODIMENTS

In one aspect the present invention discloses a polypeptide (protein) which is capable of binding immunoglobulins or immunoglobulin-containing proteins. This polypeptide comprises six or more domains (monomers) of protein Z or the C domain of protein A or a functional variant thereof. The number of domains can advantageously be from six to eight. The polypeptide can be capable of binding to regions of an immunoglobulin molecule other than the complementarity determining regions (CDR), e.g. the Fc region. The polypeptide can in the latter case be an Fc-fragment binding polypeptide. Examples of immunoglobulins that can be bound by the polypeptide are IgG, IgA and IgM. Examples of immunoglobulins that can be bound include conjugates of immunoglobulins with e.g. pharmaceutically active substances or labels useful in analysis or diagnostics. Another example is conjugates of immunoglobulins with polymers such as polyethylene glycol (PEG).

In certain embodiments, at least one of the domains, e.g. all the domains, comprises at least 80%, such as at least 90%, at least 95%, at least 99% or 100% of the sequence defined by SEQ ID NO: 1 (the Z protein), SEQ ID NO: 2 (N23T mutation of the Z protein), SEQ ID NO: 5 (a monomer unit derived from the Z protein), SEQ ID NO:6 (a monomer unit derived from the N23T mutation of the Z protein), SEQ ID NO:7 (a monomer unit derived from the C domain of protein A) or SEQ ID NO:8 (the C domain of protein A).

In some embodiments, in at least one of the domains, the amino acid residue at the position corresponding to position 23 in SEQ ID NO: 1 or 2 is a threonine. Advantageously, this amino acid residue can be a threonine in all the domains of the polypeptide. This mutation improves the alkali stability of the polypeptide and makes it possible to clean separation matrices comprising the polypeptide in alkali (e.g. NaOH) solutions of up to 0.5 or 1.0 M concentration.

In certain embodiments, the C-terminal amino acid residue of the polypeptide is a cysteine. This is advantageous for the coupling of the polypeptide to solid supports in that the nucleophilic thiol of the cysteine easily forms thioether links to supports activated with electrophilic moieties.

In some embodiments, the po

In some embodiments, the domains of the polypeptide are linked by elements (linkers) which comprise up to about 15 amino acid residues, such as e.g. 6-10 amino acid residues. The linking elements can e.g. comprise a sequence selected from the group consisting of VDAKFD (SEQ ID NO: 9), VDAKFN (SEQ ID NO: 10), QAPKVDAKFD (SEQ ID NO: 11) and QAPKVDAKFN (SEQ ID NO: 12). When used in Protein Z multimers, these linking groups are compatible with the binding functionality of the multimers. If the linkers do not contain any asparagine, which is the case for the VDAKFD (SEQ ID NO: 9) and QAPKVDAKFD (SEQ ID NO: 11) sequences, the alkali stability of the multimers can be further improved. lypeptide has a sequence as described by SEQUENCE ID NO:4 or alternatively comprises at least 80%, such as at least 90%, at least 95% or at least 99% of SEQUENCE ID NO: 4:

AQGTVDAKFDKEQQNAFYEILHLPNLTEEQRNAFIQSLKDDPSQSANLLA

EAKKLNDAQAPKVDAKFDKEQQNAFYEILHLPNLTEEQRNAFIQSLKDDP

SQSANLLAEAKKLNDAQAPKVDAKFDKEQQNAFYEILHLPNLTEEQRNAF

IQSLKDDPSQSANLLAEAKKLNDAQAPKVDAKFDKEQQNAFYEILHLPNL

TEEQRNAFIQSLKDDPSQSANLLAEAKKLNDAQAPKVDAKFDKEQQNAFY

EILHLPNLTEEQRNAFIQSLKDDPSQSANLLAEAKKLNDAQAPKVDAKFD

KEQQNAFYEILHLPNLTEEQRNAFIQSLKDDPSQSANLLAEAKKLNDAQA

PKC

In one aspect the present invention discloses a separation matrix which comprises a polypeptide as described above, coupled to a solid support. The polypeptide can be covalently coupled to the support, optionally via a spacer which can e.g. be a C1-C8 hydrocarbon, ether, thioether or amine structure with or without one or more substituents such as hydroxyl groups.

In certain embodiments, the polypeptide is coupled to the solid support via thioether bonds. If the C-terminal amino acid residue of the polypeptide is cysteine, the thiol group of this cysteine can advantageously be used for coupling with electrophilic activated groups on the support. If the C-terminal cysteine is the only cysteine in the polypeptide, this mode of coupling will give a single-point attachment of the polypeptide, which improves accessibility of the polypeptide. In consequence, the polypeptide is in certain embodiments coupled to the solid support by single-point attachment, e.g. via thioether bonds.

In some embodiments, the content of the polypeptide in the separation matrix is 7-15 mg/ml, such as 10-15 mg/ml or above 10 mg/ml. Generally, a high polypeptide content gives a high binding capacity for immunoglobulins and immunoglobulin-containing proteins.

In certain embodiments the solid support comprises a polysaccharide, e.g. dextran, pullulan, alginate, gellan gum, carrageenan, agar or agarose. The polysaccharide can specifically be agarose or a derivative of agarose.

In some embodiments the solid support is cross-linked. The cross-links can be of covalent character and may e.g. comprise ether groups such as betahydroxyl ether groups. Such groups can be introduced by crosslinking with e.g. epihalohydrins (e.g. epichlorohydrin), diepoxides and with reagents that can be converted to epoxides or halohydrins. An example of the latter is allyl halides or allylgylcidyl ether which can be reacted with e.g. agarose to form pendant allyl groups which can be converted to epoxides or halohydrins e.g. by reaction with bromine. The pendant epoxides or halohydrins can then be used for cross-linking. An advantage of using betahydroxyl ether cross-links is that chemically stable cross-links with minimal non-specific interactions with proteins can be formed. It is however also possible to use many other cross-linking reagents like divinylsulphone, diisocyanates, diacid chlorides, chlorotriazines etc. In an advantageous embodiment the solid support is agarose which has been crosslinked according to the teachings of U.S. Pat. No. 6,602,990, which produce a material of high rigidity, particularly suitable for use at high flow rates and back pressures.

In certain embodiments, the solid support comprises or consists of spherical or essentially spherical beads. Such solid supports are well suited for use in chromatography and other separation techniques. The beads can have a (volume weighted) average diameter of 100 nm to 500 micrometers, with beads having an average diameter of 30-100 micrometers being particularly suitable for large scale chromatographic separations. The beads can also have an average diameter of 1-30 micrometers, which is suitable for high resolution small a scale and analytical chromatography separations. Beads in the 0.1 to 1 micrometer size range are useful e.g. for use in immunoassays like lateral flow assays.

In an alternative embodiment, the solid support comprises or consists of a membrane or a porous monolith. The membrane may be a microfiltration membrane, e.g. comprising a cellulosic polymer, a polysulfone or a polyethersulfone. In some embodiments, the solid support is porous. The porosity can be expressed as a Kay or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. By definition, both Kd and Kay values always lie within the range 0-1. The Kay value can advantageously be 0.6-0.95, e.g. 0.7-0.90 or 0.6-0.8, as measured with dextran of Mw 110 kDa as a probe molecule. An advantage of this is that the support has a large fraction of pores able to accommodate both the polypeptides of the invention and immunoglobulins binding to the polypeptides and to provide mass transport of the immunoglobulins to and from the binding sites.

In one aspect the present invention discloses a method of separating one or more immunoglobulins or immunoglobulin-containing proteins from other solutes in a liquid. This method comprises:

(a) contacting the liquid with a separation matrix as described above;

(b) allowing the immunoglobulins or immunoglobulin-containing proteins to adsorb to the matrix by interaction with the polypeptides;

(d) recovering said immunoglobulins or immunoglobulin-containing proteins by contacting the matrix with an eluent which releases the immunoglobulins or immunoglobulin-containing proteins, or recovering at least one of said other solutes from the liquid after adsorption of immunoglobulins or immunoglobulin-containing proteins from said liquid.

The method can involve bind-elute chromatography with the immunoglobulin or the immunoglobulin-containing protein as the target, in which case step (d) can involve contacting the matrix with an eluent and recovering the immunoglobulin or immunoglobulin-containing protein from the eluate (i.e. the eluent after contacting with the matrix). Alternatively, the method can be used to remove immunoglobulins from other target solutes (e.g. proteins) and then the method can be e.g. performed in flow-through mode, where step (d) involves recovering these target solutes from the liquid (in the flow-through) after contacting the matrix. A particular advantage of using the matrix with the polypeptide of the invention is that the binding capacity for immunoglobulins and immunoglobulin-containing proteins is very high, which is highly important for the process economy.

In certain embodiments the method also comprises a step (c) of washing the separation matrix with the immunoglobulins or immunoglobulin-containing proteins adsorbed or bound to the polypeptides. This step can be undertaken before step (d) and improves the selectivity of the method in that loosely attached impurities can be washed off before elution and recovery of the immunoglobulins or immunoglobulin-containing proteins.

In some embodiments, the method further comprises a step (e) of cleaning the matrix with a solution comprising NaOH at a concentration of up to about 1 M, e.g. up to about 0.5 M, 0.1-0.5 M or 0.3-0.5 M. A high NaOH concentration is desirable as the cleaning efficiency is improved considerably.

In certain embodiments, steps (a)-(e) can be repeated at least 20 times, such as at least 50 or at least 90 times or 20-100 times, such as 20-90, 50-100, 50-90 or 20-50 times. A separation cycle can be defined as a single instance of applying steps (a)-(e) and it is highly desirable to be able to perform a large number of cycles on a column or a batch of separation matrix. Preferably, at least 70%, such as at least 80% or 90%, of the initial IgG-binding capacity of the matrix should be retained after the last cycle.

EXAMPLES

Mutagenesis of Protein

Site-directed mutagenesis was performed by a two-step PCR using oligonucleotides coding for the asparagine replacement. As template a plasmid containing a single domain of either Z or C was used. The PCR fragments were ligated into an E. coli expression vector (pGO). DNA sequencing was used to verify the correct sequence of inserted fragments.

To form multimers of Z(N23T) an Acc I site located in the starting codons (GTA GAC) of the C or Z domain was used, corresponding to amino acids VD. pGO Z(N23T)1 were digested with Acc I and CIP treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.->25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing Z(N28A)2. Positive clones were verified by DNA sequencing.

Construct Expression and Purification

The constructs were expressed in the bacterial periplasm by fermentation of *E. coli* K12 in standard media. After fermentation the cells were heat-treated to release the periplasm content into the media. The constructs released into the medium were recovered by microfiltration with a membrane having a 0.2 μm pore size.

Each construct, now in the permeate from the filtration step, was purified by affinity. The permeate was loaded onto a chromatography medium containing immobilized IgG. The loaded product was washed with phosphate buffered saline and eluted by lowering the pH.

The elution pool was adjusted to a neutral pH and reduced by addition of dithiothreitol. The sample was then loaded onto an anion exchanger. After a wash step the construct was eluted in a NaCl gradient to separate it from any contaminants. The elution pool was concentrated by ultrafiltration to 40-50 mg/ml.

The purified ligands were analyzed with LC-MS to determine the purity and to ascertain that the molecular weight corresponded to the expected (based on the amino acid sequence).

Activation

The base matrix used was either (A) rigid cross-linked agarose beads of 85 micrometers (volume-weighted) average diameter, prepared according to the methods of U.S. Pat. No. 6,602,990 and with a pore size corresponding to an inverse gel filtration chromatography Kay value of 0.70 for dextran of Mw 110 kDa, according to the methods described in Gel Filtration Principles and Methods, Pharmacia LKB Biotechnology 1991, pp 6-13 or (B) rigid crosslinked agarose beads of the same type but having average diameter 65 micrometers an a Kay value of 0.705 for dextran of Mw 110 kDa.

25 mL (g) of drained base matrix, 10.0 mL distilled water and 2.02 g NaOH (s) was mixed in a 100 mL flask with mechanical stiffing for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750. All buffers used in the experiments had been degassed by nitrogen gas for at least 5-10 mM The ligand content of the gels could be controlled by varying the concentration of the ligand solution.

After immobilization the gels were washed 3×GV with distilled water. The gels+1 GV 10.1 M phosphate/1 mM EDTA/10% thioglycerol pH 8.61 was mixed and the tubes were left in a shaking table at room temperature over night. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

Example 1

Prototype

Mutant Z(N23T)6 (SEQ ID NO: 4): ligand hexamers containing six copies of protein Z, each containing the N23T substitution (Z(N23T)6), on base matrix (A) with ligand density of 7.7 and 14.5 mg/ml.

Mutant Z(N23T)6 (SEQ ID NO: 4): ligand hexamers containing six copies of protein Z, each containing the xx substitution (Z(N23T)6), on base matrix (B) with ligand density of 11.3 mg/ml.

Mutant Z(N23T)4 (SEQ ID NO: 3): ligand tetramers containing four copies of protein Z, each containing the N23T substitution (Z(N23T)4), on base matrix (A) with ligand density of 7.9, 14.5 and 14.8 mg/ml.

2 ml of resin packed in TRICORN™ 5 100 column.

Protein

Gammanorm 165 mg/ml (Octapharma), diluted to 1 mg/ml in Equilibration buffer.

Equilibration Buffer

APB Phosphate buffer 20 mM+0.15 M NaCl, pH 7,4 (Elsichrom AB)

Adsorption Buffer

APB Phosphate buffer 20 mM+0.15 M NaCl, pH 7.4 (Elsichrom AB).

Elution buffers

Citrate buffer 0.1 M, pH 6.
Citrate buffer 0.1 M, pH 3.

CIP 0.1 M NaOH.

Experimental Details and Results:

The breakthrough capacity was determined with an ÄKTAExplorer 10 system at a residence time of 2.4 minutes. Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with equilibration buffer until a UV signal of 20% of maximum absorbance at flow rate 0.5ml/min. The protein was eluted with a linear gradient over 10 column volumes starting at pH 6.0 and ending at pH 3.0 at a flow rate of 0.5 ml/min. Then the column was cleaned with 0.1M NaOH at flow rate 0.5 ml/min and re-equilibrated with equilibration buffer prior to cleaning with 20% ethanol. The last step was to check the sample concentration by loading sample through the bypass column until a 100% UV signal was obtained.

For calculation of breakthrough capacity at 10%, equation below was used. That is i.e. the amount of IgG that is loaded onto the column until the concentration of IgG in the column effluent is 10% of the IgG concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
A(V)=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) at 10% breakthrough was calculated and the appearance of the curve was studied. The curve was also studied regarding binding, elution and CIP peak. The dynamic binding capacity (DBC) was calculated for 5, 10 and 80% breakthrough.

Some examples are shown in Table 1.

TABLE 1

Capacity data for Z6 and Z4, using 1 mg/ml IgG dissolved in 20 mM PBS + 0.15M NaCl buffer, pH 7.4.

| Prototype | Qb10 (mg/ml resin) | Qb80 (mg/ml resin) | Residence time (min) | Ligand density (mg/ml) |
|---|---|---|---|---|
| Z(N23T)6 A | 35.1 | 62.7 | 2.4 | 7.7 |
| Z(N23T)6 A | 53.4 | 68.7 | 6.0 | 7.7 |
| Z(N23T)6 A | 64.5 | 74.5 | 10.0 | 7.7 |
| Z(N23T)6 A | 31.2 | 80.6 | 2.4 | 14.5 |
| Z(N23T)6 A | 61.8 | 102.6 | 6.0 | 14.5 |
| Z(N23T)6 A | 76.7 | 103.4 | 10.0 | 14.5 |
| Z(N23T)6 B | 47.0 | 76.9 | 2.4 | 11.3 |
| Z(N23T)6 B | 68.0 | 82.8 | 6.0 | 11.3 |
| Z(N23T)4 A | 35.5 | 49.0 | 2.4 | 7.9 |
| Z(N23T)4 A | 35.4 | 83.0 | 2.4 | 14.8 |
| Z(N23T)4 A | 63 | 95 | 6.0 | 14.8 |
| Z(N23T)4 A |  |  | 10.0 | 14.8 |
| Z(N23T)4 A | 39.4 | 83.8 | 2.4 | 14.5 |
| Z(N23T)4 A | 66.1 | 91.0 | 6.0 | 14.5 |
| Z(N23T)4 A | 77 | 92 | 10.0 | 14.5 |

Example 2

The purified tetrameric and hexameric ligands Z(N23T)4 (SEQ ID NO: 3) and Z(N23T)6 (SEQ ID NO: 4) were immobilized on Biacore CM5 sensor chips (GE Healthcare, Sweden) in an amount sufficient to give a signal strength of about 1000RU in a Biacore instrument (GE Healthcare, Sweden). To follow the IgG binding capacity of the immobilized surface 1 mg/ml hIgG (Gammanorm, as described above) was flowed over the chip and the signal strength was noted. The surface was then cleaned-in-place (CIP), i.e. flushed with 500 mM NaOH for 10 minutes. This was repeated for 96 cycles and the immobilized ligand alkaline stability was followed as the relative loss of IgG binding capacity (signal strength) after each cycle. The results are shown in FIG. 1 and indicate that the alkali stability of the hexamer Z(N23T)6 (Z6, upper curve) is significantly better than for the tetramer Z(N23T)4 (Z4, lower curve).

This written description uses examples to disclose the invention, including the best mode, and also to enable any person skilled in the art to practice the invention, including making and using any devices or systems and performing any incorporated methods. It should be noted that features from different embodiments can be combined. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A polypeptide capable of binding immunoglobulins or immunoglobulin-containing proteins, wherein the polypeptide comprises six or more domains that are selected from a group consisting of: protein Z or the C domain of protein A, and a single terminal coupler that can be coupled with a support to form a spacer that comprises C1-C8 hydrocarbon, ether, thioether or amine structure with or without one or more substituents, wherein in each of the domain, the amino acid residue at positon 28 is asparagine and in at least one of the domains, the amino acid residue at position 23 is a threonine.

2. The polypeptide of claim 1, wherein at least one domain comprises the sequence defined by SEQ ID NO: 1, SEQ ID NO: 2, SEQ ID NO:5, SEQ ID NO: 6, SEQ ID NO:7 or SEQ ID NO:8.

3. The polypeptide of claim 1, which is an Fc fragment-binding polypeptide.

4. The polypeptide of claim 1, wherein said domains are linked by elements comprising up to about 15 amino acids.

5. The polypeptide of claim 4, wherein the linking element comprises a sequence selected from the group consisting of VDAKFD (SEQ ID NO: 9), VDAKFN (SEQ ID NO: 10), QAPKVDAKFD (SEQ ID NO: 11) and QAPKVDAKFN (SEQ ID NO: 12).

6. The polypeptide of claim 1, which comprises six to eight domains of protein Z.

7. The polypeptide of claim 1, which comprises six to eight C-domains of protein A.

8. The polypeptide of claim 1, wherein the terminal coupler is a C-terminal amino acid residue cysteine.

9. A separation matrix comprising the polypeptide of claim 1 coupled to a solid support via the single terminal coupler to form a single-point attachment.

10. The separation matrix of claim 9, wherein said polypeptide is coupled via thioether bonds.

11. The separation matrix of claim 9, wherein the content of said polypeptide is 7-15 mg/ml.

12. The separation matrix of claim 9, wherein the solid support comprises a polysaccharide.

13. The separation matrix of claim 9, wherein the solid support is cross-linked.

14. The separation matrix of claim 9, wherein the solid support comprises spherical or essentially spherical beads, having a volume-weighted average diameter of 100 nm - 500 micrometers.

15. The separation matrix of claim 9, wherein the solid support has a porosity corresponding to a Kay value of 0.6 -0.95 as measured with dextran of Mw 110 kDa under inverse size exclusion chromatography conditions.

16. A polypeptide capable of binding immunoglobulins or immunoglobulin-containing protein, as defined by SEQ ID NO: 4.

17. A polypeptide capable of binding immunoglobulins or immunoglobulin-containing protein, wherein the polypeptide comprises six or more domains of protein Z or the C domain of protein A and at least one domain comprises the sequence defined by SEQ ID NO: 1, SEQ ID NO: 2, SEQ ID NO:5, SEQ ID NO: 6, SEQ ID NO:7 or SEQ ID NO:8 and a single terminal coupler that can be coupled with a support to form a spacer that comprises C1-C8 hydrocarbon, ether, thioether or amine structure with or without one or more substituents.

18. A method of separating one or more immunoglobulins or immunoglobulin-containing proteins from other solutes in a liquid, which method comprises:
  (a) contacting the liquid with the separation matrix of claim 9;
  (b) allowing said immunoglobulins or immunoglobulin-containing proteins to adsorb to the matrix by interaction with the polypeptides while having the other solutes remain in the liquid; and
  (d) recovering said immunoglobulins or immunoglobulin-containing proteins by contacting the matrix with an eluent which releases the immunoglobulins or immunoglobulin-containing proteins, or recovering at least one of said other solutes from the liquid after adsorption of immunoglobulins or immunoglobulin-containing proteins to the matrix.

19. The method of claim 18, further comprising, before step (d), a step (c) of removing the other solutes and washing the separation matrix of said adsorbed immunoglobulins or immunoglobulin-containing proteins.

20. The method of claim 18, furthercomprising after step (d), a step (e) of cleaning the matrix with a solution comprising NaOH at a concentration of up to about 0.5 M.

21. The method of claim 20, wherein steps (a) - (e) are repeated at least 50 times.

* * * * *